US011517259B2

(12) United States Patent
Olivarez

(10) Patent No.: US 11,517,259 B2
(45) Date of Patent: Dec. 6, 2022

(54) TEMPERATURE-SENSING FACEMASK WITH DISPLAY

(71) Applicant: Antionette Olivarez, Porter Ranch, CA (US)

(72) Inventor: Antionette Olivarez, Porter Ranch, CA (US)

( * ) Notice: Subject to any disclaimer, the term of this patent is extended or adjusted under 35 U.S.C. 154(b) by 0 days.

(21) Appl. No.: 17/163,806

(22) Filed: Feb. 1, 2021

(65) Prior Publication Data
US 2022/0240853 A1  Aug. 4, 2022

(51) Int. Cl.
| | |
|---|---|
| *A61B 5/00* | (2006.01) |
| *A61B 5/01* | (2006.01) |
| *G09G 3/20* | (2006.01) |
| *A41D 13/11* | (2006.01) |

(52) U.S. Cl.
CPC ........ *A61B 5/6803* (2013.01); *A41D 13/1161* (2013.01); *A61B 5/01* (2013.01); *G09G 3/20* (2013.01)

(58) Field of Classification Search
CPC ............ A41D 13/1161; A41D 13/1115; A41D 13/1281; A61B 5/01; A61B 5/6803; G09G 3/20; G09G 5/02; G09G 2380/08
See application file for complete search history.

(56) References Cited

U.S. PATENT DOCUMENTS

| | | | | |
|---|---|---|---|---|
| 4,875,477 A | * | 10/1989 | Waschke | A61B 5/6803 128/206.26 |
| 6,199,550 B1 | * | 3/2001 | Wiesmann | G08B 21/0453 128/204.23 |
| 7,296,570 B2 | * | 11/2007 | Hutchinson | A61M 16/0688 128/857 |
| 7,298,535 B2 | * | 11/2007 | Kuutti | G08B 21/02 359/13 |
| 8,911,380 B1 | * | 12/2014 | Feldman | A61B 5/0878 600/536 |
| 10,219,743 B2 | * | 3/2019 | Larsen | A61B 5/01 |
| 10,561,863 B1 | * | 2/2020 | Dashevsky | A61B 5/01 |
| 10,772,371 B1 | * | 9/2020 | Sabin | A42B 1/008 |
| 10,881,157 B1 | * | 1/2021 | Anderson | A41D 13/1107 |
| 10,905,904 B2 | * | 2/2021 | Johnson | A41D 13/1218 |
| 11,096,438 B1 | * | 8/2021 | Sabin | A41D 13/0051 |
| 2004/0163648 A1 | * | 8/2004 | Burton | A61M 16/0694 128/204.21 |
| 2010/0078025 A1 | * | 4/2010 | Grilliot | A62B 7/02 128/204.21 |
| 2011/0087084 A1 | * | 4/2011 | Jeong | A61B 5/14546 600/300 |
| 2015/0148681 A1 | * | 5/2015 | Abreu | A61B 5/6821 600/474 |

(Continued)

*Primary Examiner* — May A Abouelela
(74) *Attorney, Agent, or Firm* — Bruce A. Lev

(57) ABSTRACT

A temperature-sensing face covering, such as a facemask or a face shield, with a temperature sensor and display unit therein to provide for hands free temperature readings that go wherever the individual goes and continue to measure the individual's temperature throughout the day. The temperature-sensing face covering is simple and does not require the sites of work or other places to have any additional equipment, and provides continual readings that could very easily change throughout the day and be missed because at the beginning of the day the individual did not have a fever.

1 Claim, 2 Drawing Sheets

(56) References Cited

U.S. PATENT DOCUMENTS

| | | | | |
|---|---|---|---|---|
| 2016/0199674 | A1* | 7/2016 | Johnson | A43B 3/18 |
| | | | | 2/457 |
| 2017/0065784 | A1* | 3/2017 | Mashal | A61M 16/0683 |
| 2017/0347890 | A1* | 12/2017 | Lai | A61B 5/0008 |
| 2018/0311517 | A1* | 11/2018 | Patil | A62B 18/02 |
| 2018/0372555 | A1* | 12/2018 | Allen, Sr. | G01K 13/00 |
| 2019/0254538 | A1* | 8/2019 | Erdman | A61B 5/6803 |
| 2020/0114103 | A1* | 4/2020 | Richard | A61B 5/082 |
| 2020/0359886 | A1* | 11/2020 | Azar | G02B 27/0172 |
| 2021/0086005 | A1* | 3/2021 | O'Brien | A62B 9/006 |
| 2021/0093205 | A1* | 4/2021 | Zhao | A61B 5/6803 |
| 2021/0282665 | A1* | 9/2021 | White | A61B 5/0816 |
| 2021/0368885 | A1* | 12/2021 | Atri | A42B 3/225 |
| 2022/0071317 | A1* | 3/2022 | Isgar | A42B 3/30 |

* cited by examiner

TEMPERATURE-SENSING FACEMASK WITH DISPLAY

CROSS-REFERENCE TO RELATED APPLICATION

The present application is related to and claims priority from prior provisional application Ser. No. 63/091,640, filed Oct. 14, 2020, the entire application of which is incorporated herein by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of face coverings and more specifically relates to a temperature-sensing face shield or facemask.

2. Description of the Related Art

Facemasks are common items worn worldwide during flu season and pandemics. Wearing a facemask helps prevent the wearer from spreading any infectious agent(s) he or she may currently have, including bacteria and viruses. They may also provide some level of protection against coming into contact with an infectious agent shed by another person.

The guidelines issued by the United States Food and Drug Administration (FDA) include using temperature measurements as part of an assessment to determine if a person has an illness that commonly causes elevated body temperature, such as COVID-19. The United States Center for Disease Control and Prevention (CDC) recommends using indications of a fever equal to or higher than 100.4° F. as a guide to check for possible infection.

Currently, many places are requiring everyone who enters to stop at the entrance and have their temperature taken. This requires many places of business to set up a temperature-check local and system, and buy temperature-sensing equipment. However, an individual could be afebrile when they enter the building, but develop a fever over the course of the day and not know he or she was febrile because he or she was afebrile when checked earlier in the day. Alternately, people may be walking around in areas where such temperature checks are not performed and never realize they are ill. Or they walk about not knowing that they are ill. An easy way for individuals to monitor their temperature on the go throughout the day would provide an early warning indicator of illness.

Various attempts have been made to solve the problems that may be found in the related art but have thus far been unsuccessful. A need exists for a reliable temperature-sensing face covering to avoid the above-mentioned problems.

BRIEF SUMMARY OF THE INVENTION

In view of the foregoing disadvantages inherent in the known art, the present invention provides a novel temperature-sensing face covering. The general purpose of the present invention, which will be described subsequently in greater detail, is to, provide a temperature sensor on a facemask or face shield. Such temperature-sensing facemasks and face shields provide for hands free temperature readings that go wherever the individual goes, and continue to measure the individual's temperature throughout the day. The temperature-sensing face covering is simple and does not require the sites of work or other places to have any additional equipment, and provides continual readings that could very easily change throughout the day and be missed because at the beginning of the day the individual did not have a fever.

Such masks are also useful in the healthcare fields. Individuals who work in healthcare frequently are exposed to viruses and other droplet or airborne illnesses. The ability for the individual to wear their thermometer provides for rapid assessment and intervention, both in routine healthcare situations and crisis pandemic situations.

The features of the invention that are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures that accompany the written portion of this specification illustrate embodiments and method(s) of use for the present invention, a temperature-sensing face covering, constructed and operative according to the teachings of the present invention.

The various embodiments of the present invention will hereinafter be described in conjunction with the appended drawings.

DETAILED DESCRIPTION

As discussed above, embodiments of the present invention relate to a temperature-sensing face covering and more particularly to a facemask with a temperature sensor.

Generally speaking, the temperature-sensing facemask with display, as presently claimed, is a novel facemask that both detects the wearer's temperature, and provides a display to alert the wearer and those around him or her if the wearer's temperature rises.

Figure 1:
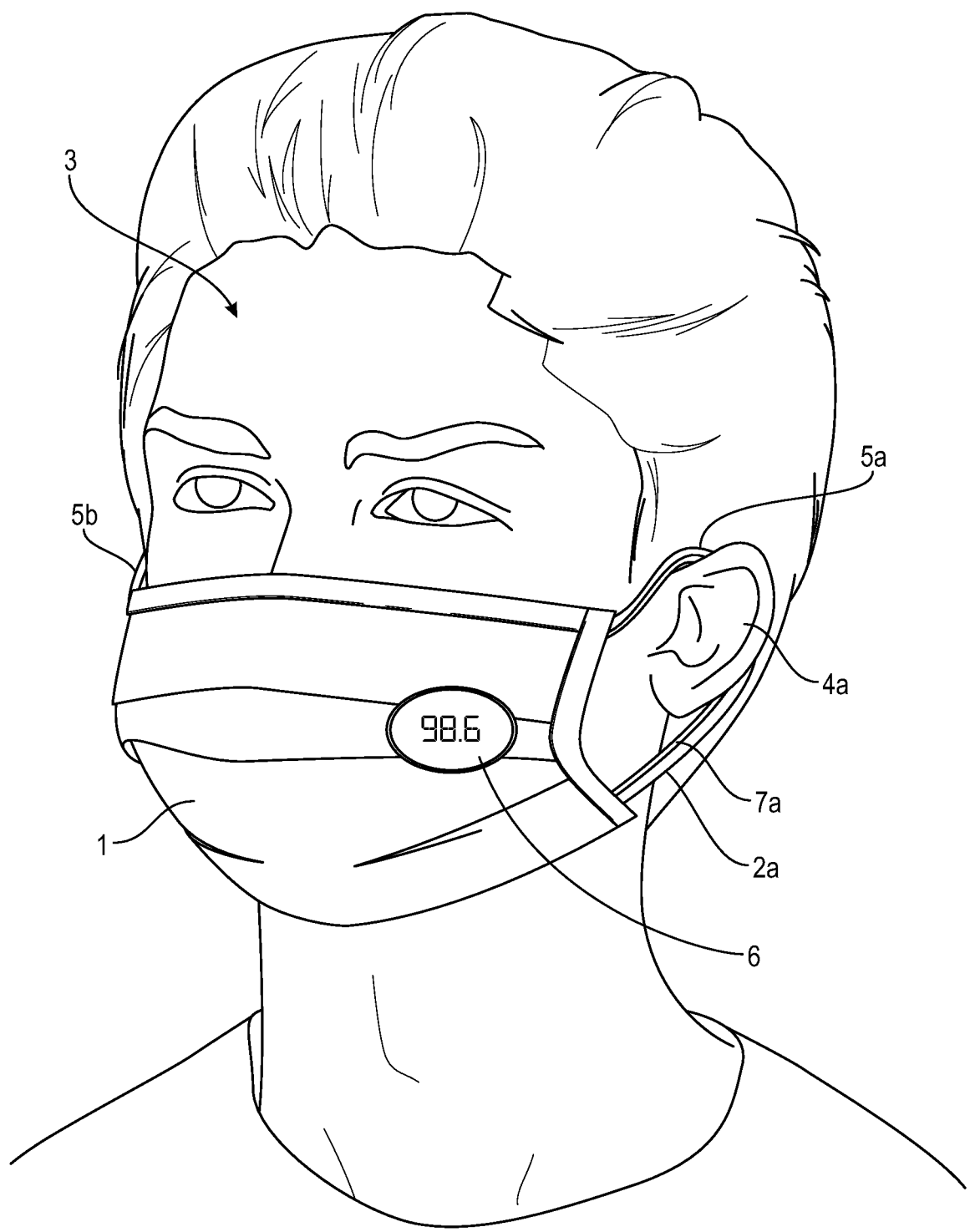
FIG. 1 shows a perspective view illustrating a temperature-sensing facemask according to an embodiment of the present invention.
Figure 2:
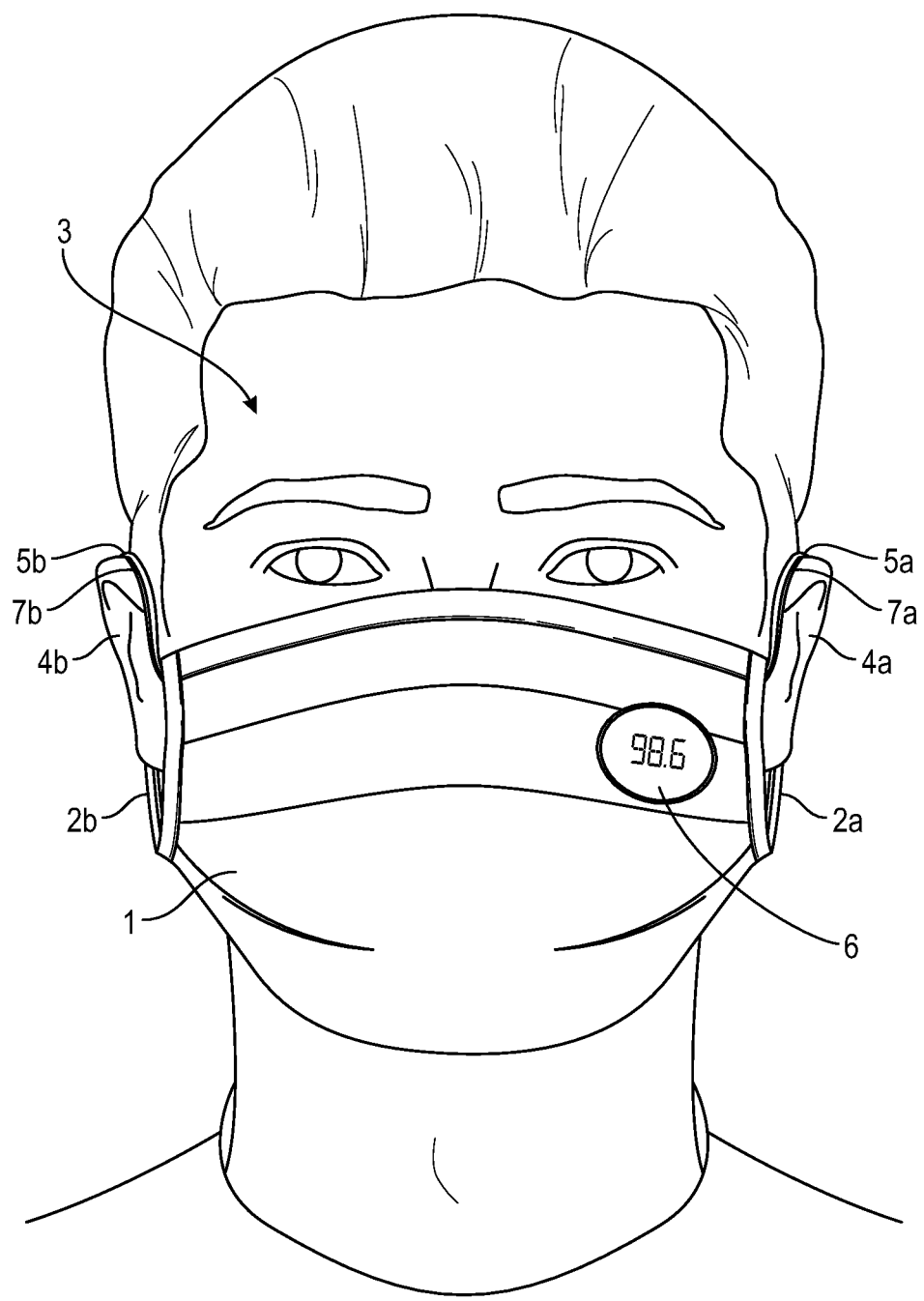
FIG. 2 shows a perspective view illustrating a temperature-sensing facemask according to an embodiment of the present invention.

Referring now to the drawings FIGS. 1-2, the temperature-sensing facemask includes a mask portion 1 and two earloops 2a, 2b, one on each side of the mask portion 1, to secure the mask portion 1 to the wearer's face 3 via the wearer's ears 4a, 4b. At least one of the earloops 2a, 2b has at least one temperature sensor 5 embedded therein or attached thereon. Preferably both the left earloop 2a and the right earloop 2b each have at least on temperature sensor 5a, 5b embedded therein respectively, so that at least one temperature sensor 5a, 5b will receive a consistent reading even if one earloop 2a, 2b is not flush against the wearer's ears 4a, 4b. The mask portion 1 and earloops 2a, 2b may come in a variety of sizes, colors, and patterns.

The mask portion 1 has an emblem, marker, or other display 6 that either displays the current temperature reading. Alternately, the emblem, marker, or other display 6 may display a color if the wearer's temperature is below 100.4° F. and change colors to display a different color if the wearer's temperature is over 100.4° F. The emblem, marker, or other display 6 may also both display the current temperature reading from the temperature sensor 5 and a color indication of whether or not the current temperature reading is below or above 100.4° F. The emblem, marker, or other display 6 may be located on either side of the mask portion 1, and may come in a variety of sizes and colors.

The temperature sensor(s) 5 may likewise be an infrared temperature sensor. A small lip 7a, 7b on the earloop 2a, 2b may separate the infrared temperature sensor 5 from the wearer's skin 3, or the infrared temperature sensor 5 may directly abut the wearer's skin 3, so long as the temperature sensor 5 is able to continually monitor the wearer's body temperature.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claim:

1. A temperature-sensing facemask with a display comprising:
   a. a nose-covering and mouth-covering mask portion having an inside side and an outside side;
   b. the display operably connected to the outside side of the mask portion so as to be visible when a user is wearing the facemask;
   c. a left earloop and a right earloop, wherein the left earloop is operably connected to a left side of the mask portion and the right earloop is operably connected to a right side of the mask portion to hold the mask portion over the user's nose and mouth when the left earloop is looped over the user's left ear and the right earloop is looped over the user's right ear;
   d. a first temperature sensor and a second temperature sensor, wherein the first temperature sensor is operably connected to or embedded within the left earloop, and the second temperature sensor is operably connected to or embedded within the right earloop to continually detect the user's body temperature,
   wherein the first temperature sensor and the second temperature sensor are operably connected to the display in order to provide a body temperature indication for the user, wherein the display is a programmable digital display that indicates the user's body temperature in numerical form, and wherein the display shows a first color when the user's body temperature is 100.4° F. or lower, and a second color when the user's body temperature is higher than 100.4° F.; and
   wherein the left earloop and the right earloop further comprise:
   e. a left earloop lip or a right earloop lip or a left earloop lip and a right earloop lip, wherein the first and second temperature sensors are operably positioned on the left earloop lip, the right earloop lip, or both left earloop and the right earloop lips so there is a gap between the first and second temperature sensors and the user's skin, and wherein the first temperature sensor and the second temperature sensor are infrared temperature sensors.

* * * * *